(12) United States Patent
Kobozev

(10) Patent No.: US 6,453,199 B1
(45) Date of Patent: Sep. 17, 2002

(54) ELECTRICAL GASTRO-INTESTINAL TRACT STIMULATOR

(76) Inventor: Valery Ivanovich Kobozev, Govorova str., 24, kv. 113, Tomsk 634057 (RU)

( * ) Notice: Subject to any disclaimer, the term of this patent is extended or adjusted under 35 U.S.C. 154(b) by 0 days.

(21) Appl. No.: 09/155,820

(22) PCT Filed: Mar. 28, 1997

(86) PCT No.: PCT/RU97/00091

§ 371 (c)(1),
(2), (4) Date: Sep. 30, 1998

(87) PCT Pub. No.: WO97/36646

PCT Pub. Date: Oct. 9, 1997

(30) Foreign Application Priority Data

Apr. 1, 1996 (RU) ............................................. 96106244
Nov. 10, 1996 (RU) ............................................. 96121950

(51) Int. Cl.⁷ ................................................. A61N 1/36
(52) U.S. Cl. ............................. 607/40; 607/133; 607/3; 607/36; 607/138; 600/302; 340/573.1
(58) Field of Search ................................. 607/133, 2, 3, 607/36, 40, 138; 128/899, 903; 600/301, 546, 302; 340/870.1, 870.01, 573.1, 573.5

(56) References Cited

U.S. PATENT DOCUMENTS

| | | | | |
|---|---|---|---|---|
| 3,682,160 A | * | 8/1972 | Murata | 600/302 |
| 3,739,279 A | * | 6/1973 | Hollis | 340/870.34 |
| 3,791,377 A | * | 2/1974 | Norby et al. | 600/302 |
| 3,971,362 A | * | 7/1976 | Pope et al. | 600/302 |
| 4,399,821 A | * | 8/1983 | Bowers | 340/573.2 |
| 4,844,076 A | * | 7/1989 | Lesho et al. | 128/903 |
| 5,193,540 A | * | 3/1993 | Schulman et al. | 607/61 |
| 5,697,384 A | * | 12/1997 | Miyawaki et al. | 128/899 |

FOREIGN PATENT DOCUMENTS

SU 0936931 * 6/1982 ................. 607/40

* cited by examiner

Primary Examiner—Kennedy Schaetzle
(74) Attorney, Agent, or Firm—Sherman D. Pernia

(57) ABSTRACT

The invention relates to medicine specifically to medical technology, and concerns electrical gastro-intestinal tract and mucous membrane stimulators. The electrical gastro-intestinal tract stimulator comprises a casing (1) with electrodes and in the form of a medicinal capsule containing a power source (4), a control unit (5) of which M outputs are connected to M electrodes (3), a device (6) for receiving signals from internal organs and/or an external transmitter, to (1–N) outputs of which are connected (1–N) inputs of the control unit (5). The electrical stimulator can contain P additional electrodes (7) provided with a coating of microelements or medicinal preparations and connected to P separate outputs of the control unit (5). The electrical stimulator can also contain a signal transmitter (10) designed to transmit signals from the device (6) for receiving signals from internal organs and/or external transmitter and control unit (5) to an external receiver for medical observation and monitoring. The dimensions of the electrical stimulator are restricted by the requirement that it be capable of being introduced into the gastro-intestinal tract orally or rectally or suitable for vaginal use.

19 Claims, 4 Drawing Sheets

ELECTRICAL GASTRO-INTESTINAL TRACT STIMULATOR

The present application is a U.S. National Stage application claiming the benefit of prior filed International Application, serial number PCT/RU97/00091, filed Mar. 28, 1997, which International Application claims a priority date of Apr. 1, 1996 based on prior filed Russian Application serial number RU96/106244.

AREA OF ENGINEERING

The invention relates to medicine, specifically to medical technology and can be used for electrical stimulation of organs of gastro-intestinal tract (GIT) and mucous membranes in abdominal surgery and for treatment of therapeutic type diseases.

BACKGROUND OF THE INVENTION

There is known in the art an apparatus with biocontrol, used in experimental researches (see M. A. Sobakin and V. A. Shepelev "Further instrumental-methodical electrical stomach stimulation providing with use of a feedback principle", /Experimental surgery and anesthesiology/—1973, vol. 2, p26), wherein pulses were sent at each positive phase of a patient's own biopotential, as received from implanted electrodes. A disadvantage of the described method of electrical GIT stimulation is the restriction of its sphere of application, which is possible only [at operated sick person] with a surgery patient, and this person must be connected to the equipment.

There is known an electrical stimulator EGS-35-1 "ENDOTON-1", it has dimensions of 395×305×100 mm and a weight of 3 kgs (see "Electrical gastro-intestinal tract stimulation", Moscow, "Medicine", 1978, A. A. Vishnevsky, A. V. Livshitz, M. P. Vilyansky). In this book the modern principles and techniques of electrical GIT organs stimulation are described. This and other external electrical GIT stimulators use a set of electrodes, one of which is a rectal or duodenal probe-electrode, other is a cutaneous one, or one bipolar electrode. A disadvantage of this kind of electrical stimulator is that the patient during a session of electrical stimulation is bound to electrical stimulator by wires, therefore, the application of electrical stimulators of that kind outside of medical establishment is difficult.

There is also known a probe-stimulator for prolonged influence on a stomach and sections of GIT within the reach of a length of connecting drain (patent RU No. 1223922, MKI A61 N 1/36, published Bulletin of Inventions of Russia (BIR) No. 14, 1986). Its disadvantage is a limited sphere of application, in that only out-patient and clinical application is possible.

There is also known an electrical stimulator containing a pulse generator, power source, electrodes, and an electrode-anode entirely covered by a conductive film of microelements with thickness no less than 10 microns (patent RU No. 2036671, MKI 61 N 1/36, published BIR No. 16, 1995). A disadvantage of this invention is that the microelements from the film run within the whole length of GIT, nor does it provide enough selectivity in treatment, or feedback between a GIT condition and the subjective sensations of a patient. This restricts the application of the electrical stimulator. On the other hand, it would be advantageous if produced models of electrical stimulators typically did not rely on such films, that complicates their application.

The most close in technical essence to the offered invention is an electrical GIT stimulator containing electrodes, and having two electrical isolated parts of a medicinal capsule, where the pulse generator and power source are placed, and which capsule is capable of moving autonomously the full length of the gastro-intestinal tract, and to influence by electrical pulses the whole length of the GIT (patent RU No. 936931 MKI A61 N 1/36, published BIR No. 23, 1982). Autonomous electrical GIT stimulator can accomplish a positive effect in treatment and prophylaxis of various diseases (see "Autonomous electrical stimulators of an organism of human and animals" Pekarsky V. V. and other, Siberian Medical University (SMU), Tomsk 1995, "Autonomous electrical GIT stimulation" Dambaev G. C. and other, Siberian gastroenterology and gepatology magazine, October 1996, V 1, No. 2). However, because of the lack of a feedback mechanism to control the operational or electrical stimulation parameters of the device in response to a condition in GIT organs relative to the subjective sensations of a patient (e.g., pains and muscular convulsions arising at passage of the device through some sections of GIT) and the limited parameters of electrical stimulation of GIT, there are a number of side-effects which contra-indicate use of the '931 device.

SUMMARY OF THE INVENTION

The object and main problem, solved by the offered invention, is an improved autonomous electrical GIT stimulator, for treatment and prevention of certain gastro-intestinal diseases. Another object is the autonomous electrical GIT stimulator having a feedback mechanism to control the operational or electrical stimulation parameters of the device in response to the subjective sensations of a patient regarding the condition of his/her internal organs. The incorporation of a feedback element provides for control of the electrical stimulator and an opportunity to change parameters of pulses according to a method of treatment, or to the subjective sensations of a patient during use of the GIT stimulator device. This is to say that the feedback element is provided as a mechanism to control the stimulator device from outside the patient's body, and to change the pulse parameters emitted by the device according to a specific treatment regimen, according to the subjective sensations of a patient his or herself, when trained in use of the GIT stimulator device. It is also an optional feature of the offered invention to increase the efficiency of a treatment regimen by the controlled release of prescribed microelements or preparations (drugs) from the stimulator device by an electrochemical means as it passes through the appropriate sections of the GIT. To increase the convenience of such use of the device replaceable electrodes with coatings of prescribed microelements or medicinal preparations can be installed on the device by the patient.

Another object of the electrical GIT is a receiver device and a control unit. The receiver device receives signals from internal organs (of the GIT) and/or an external transmitter. The outputs (1 to N) of the receiver device are connected to the inputs of the control unit. The control unit, based on a hardware or a program algorithm, sends a series of pulses to the M-electrodes of the electrical stimulator, depending on the signals (from the internal organs and/or the external transmitter) coming in from the receiver device.

Another object of the offered invention is a feedback mechanism the subjective sensations of the patient and the parameters of electrical stimulation of the GIT organs. The feedback mechanism is accomplished by adding sensors of signals to the receiver device. Signal sensors are for receiving signals from an external transmitter, from the internal GIT organs or from both. Feedback between the GIT organs and the stimulator of the physiological parameters of the GIT organs is used to adjust or correct the parameters of electrical pulses from the stimulator depending on the changes in the physiological parameters of the GIT. The receiver device may contain sensors for: pressure, a gradient (difference) of pressure, pH, acoustics, temperature, biopotential, and conductivity of stimulated tissue. Therefore, the present stimulator may adjust its output pulse parameters in response to feedback received from the sensors or by way of an external signal transmitted, for example, by the patient in response to subjective sensation.

To further increase treatment efficiency, the offered invention includes the installation of additional P-electrodes of selected microelements or medical preparations as required, into a section of the GIT stimulator. The additional P-electrodes have a coating of microelements or medicinal preparations, and are connected to the separate outputs of the control unit. In keeping with the purpose of improved treatment and prevention, and for convenience of use, replaceable P-electrodes are used in the offered electrical GIT stimulator. The additional P-electrodes can be carried out as demountable or replaceable by a user of the device.

The offered electrical GIT stimulator, comprises a casing in the form of a medicinal capsule and having surface electrodes. The casing containing a power source, a control unit, outputs connected to M-electrodes, a receiving device having outputs connected to inputs of a control unit, and a control unit. The dimensions and the shape or form of electrical stimulator are limited by the requirement of its introduction into gastro-intestinal tract orally or rectally, or of its vaginal use.

The receiver device receives signals from the internal GIT organs, an external transmitter or from both. The receiver device comprises sensors for sensing physiological parameters of motor evacuative function and current condition of GIT organs, and also signals from an external transmitter, the outputs of which being inputs of the receiver device. The sensors of the receiver device for receiving signals from internal GIT organs include: a sensor of pressure, a sensor of pressure gradient, a pH-sensor, an acoustic sensor, a sensor of temperature, a sensor of biopotential, a sensor of conductivity. Alternatively, the electrodes of the electrical stimulator can be used as the electrodes of the sensor of biopotential and of the sensor of conductivity.

The offered electrical stimulator in addition contains a signal transmitter having inputs which are connected to the outputs of the receiver device, and to a separate output of the control unit.

The control unit in the best embodiment contains a micro-controller. The micro-controller has analog-digital amplifier circuits the inputs of which are connected from the receiving device through the amplifiers to the outputs of the micro-controller device, its outputs being the M outputs of the control unit. Accordingly, the outputs of the control unit are connected to the M-electrodes of electrical stimulator. Likewise, the additional outputs of the micro-controller, being the outputs of the control unit, are connected to the additional P-electrodes.

The main positive effect, which autonomous electrical GIT stimulators have is their ability to restore the motor-evacuative function of the GIT. The offered electrical GIT stimulator, in contrast to what is known, is capable not only to move autonomously through the gastro-intestinal tract, but also to selectively influence GIT sites by intermittently applying electrical pulses to the sites, consecutively restoring functions of organs along the whole length of the GIT.

Along with the positive effect of autonomous electrical stimulation of the offered stimulator on GIT organs already proved experimentally and in a wide clinical practice, the application of the offered electrical stimulator gives a new opportunity to selectively and purposefully influence by electrical stimulation specific sections and organs of GIT. This new opportunity to increase treatment efficiency is owing to the ability to introduce prescribed medicinal preparations and microelements to the necessary GIT sections by an electrochemical way or means. The opportunity to adjust the pulse parameters of the autonomous electrical stimulator depends on a condition of internal organs appearing as a subjective sensation of a patient. Also, the opportunity to select modes of autonomous electrical stimulation depends on the character of a disease and from a current condition of GIT motor activity, and from other parameters indicative of a condition of GIT organs detected by the sensors.

The above named purposes, characteristics and advantages of the present invention will be more clear from the following detailed description, which is accompanied by the appropriate drawings.

DETAILED DESCRIPTION OF EMBODIMENTS

Figure 1:
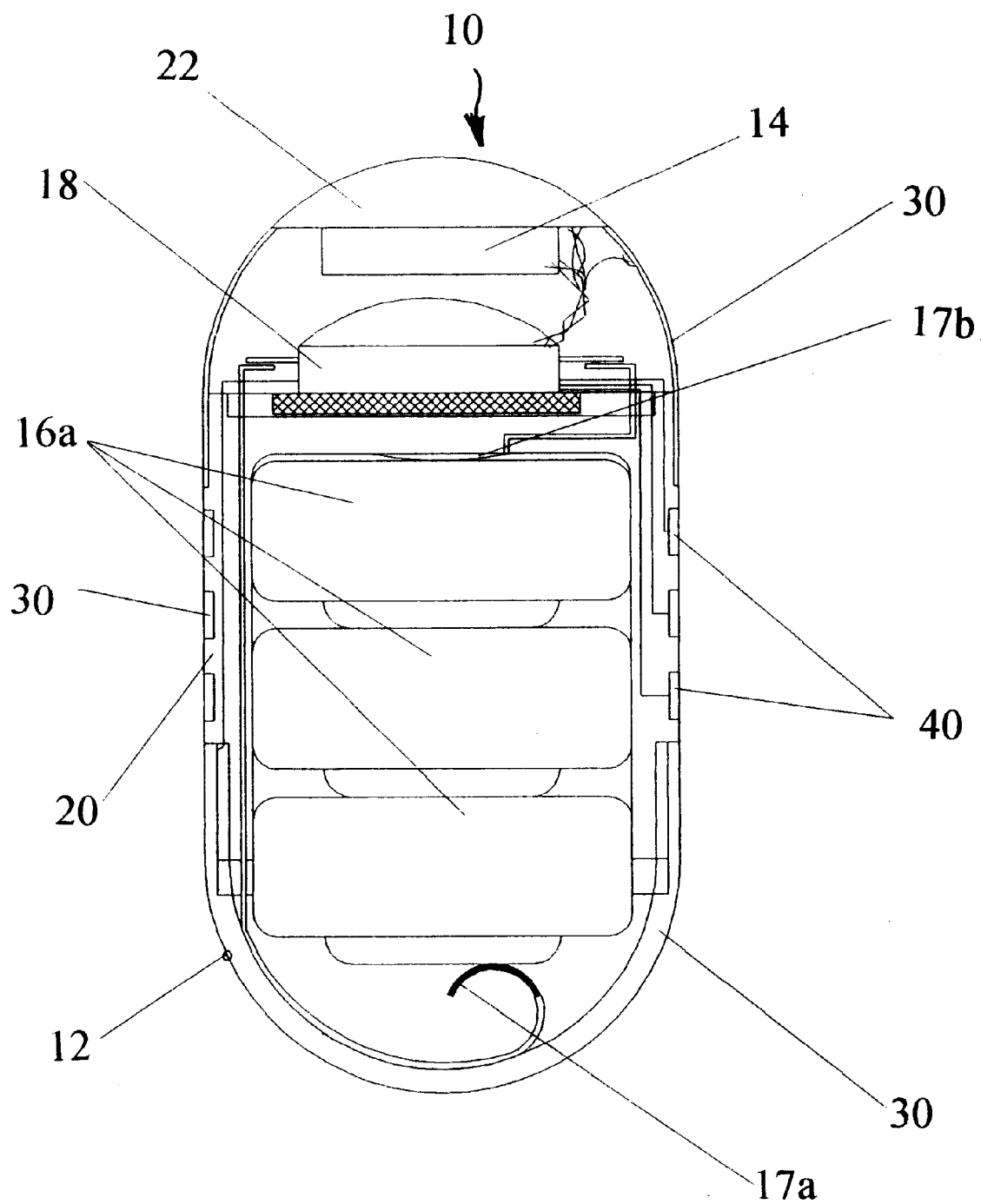
FIG. 1 is a top plan cut-away view which represents a construction of the offered electrical gastro-intestinal tract stimulator.

Referring now to the drawings, the details of preferred embodiments of the present invention are graphically and schematically illustrated. Like elements in the drawings are represented by like numbers, and similar elements are referred to by like numbers with a letter suffix.

Figure 2:
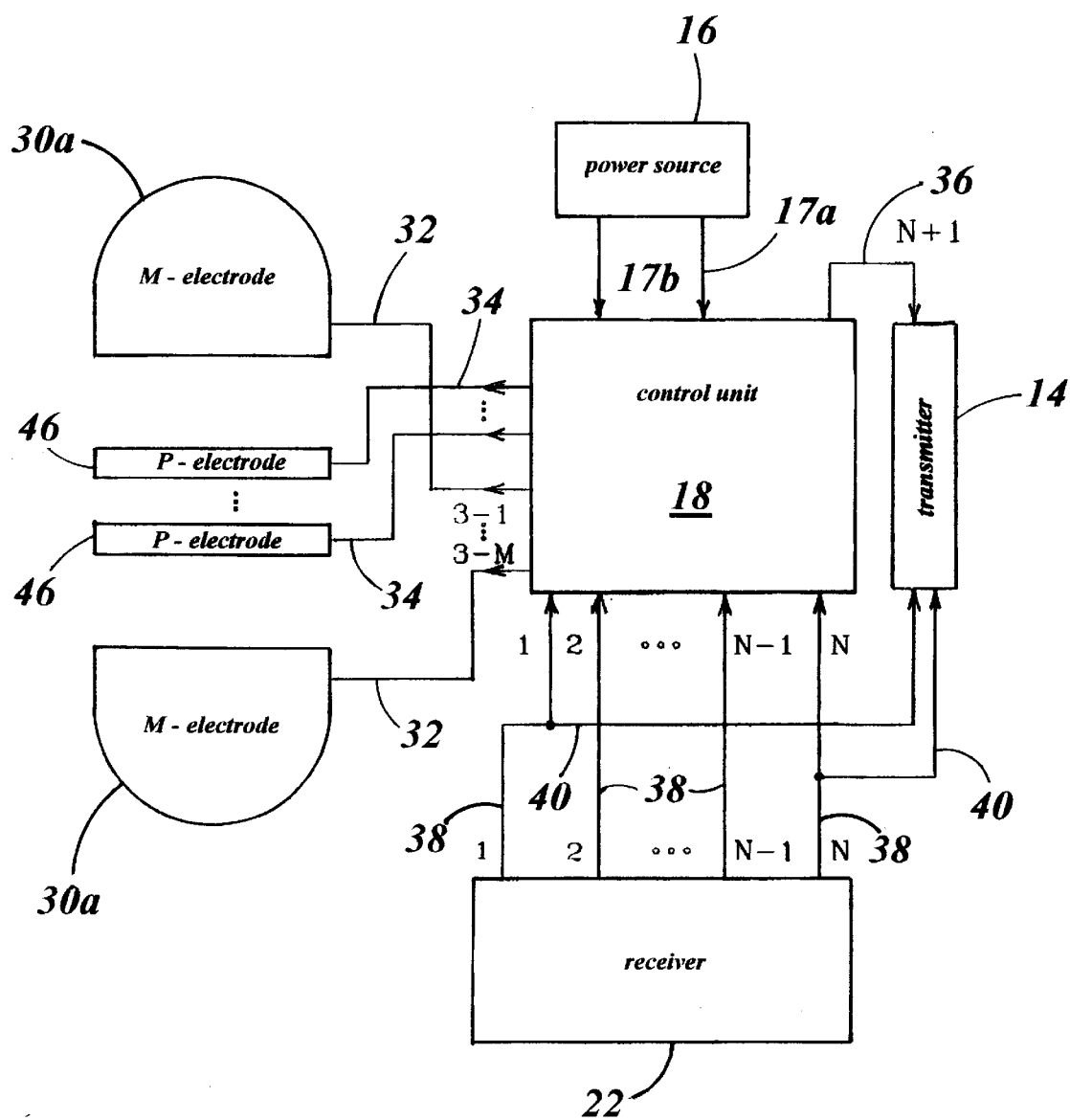
FIG. 2 is a block diagram of the offered electrical GIT stimulator.

As shown in FIG. 1, the offered electrical GIT stimulator 10 is constructed in the shape of a medicinal capsule and configured to be administered orally to a patient. Referring to FIG. 1, the offered invention comprises a housing or casing 12, a power source 16, a control unit 18, a signal transmitter 14, and a signal receiver 22. The casing 12 has M-electrodes 30 and P-electrodes 40 exposed on the outer surface of the casing 12, and a dielectric bushing 20 for electrically isolating the various electrodes and components of the stimulator 10. The power source 16 in the embodiment shown in FIG. 1 is a series of batteries 16a. The power source 16 is connected to the control unit 18 by spring contact electrical connections 17a & 17b. FIG. 2 is a block schematic showing the interconnection of the major components of the offered stimulator 10. The batteries 16a of the power source 16 are connected to the control unit 18. The control unit 18 has a plurality of controller/M-electrode connection 32 connecting it to a plurality of M-electrodes, and a plurality of controller/P-electrode connections 34 connecting it to a plurality of P-electrodes. The control unit may have more outputs to the electrodes than are shown as actually connected in the figures. Additionally the controller unit has a controller/transmitter connection 36 to the signal transmitter. The control unit 18 has controller/receiver connections 38 between itself and the signal receiver device 22. There may be more connection points between the controller and the signal receiver unit 22 than are connections 38 actually shown in the figures. The dimensions and shape of electrical GIT stimulator 10 are limited by the need to introduce it into a patient's gastro- intestinal tract orally or rectally, or for vaginal use.

Figure 3:
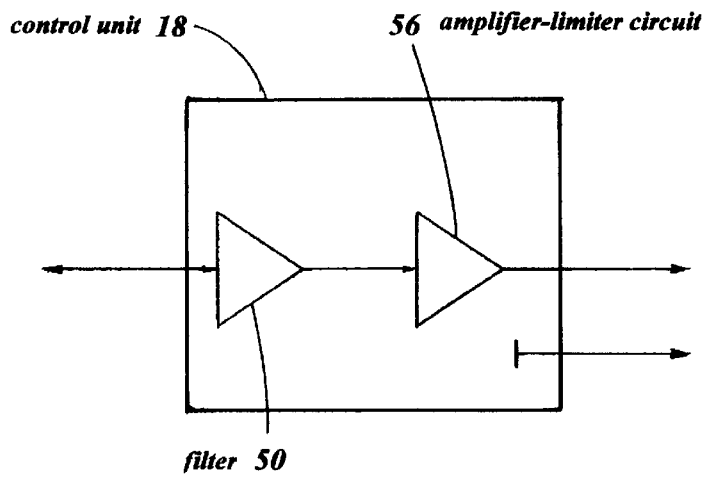
FIG. 3 is a block diagram of the control unit in the simplest embodiment with an external control input.

In the simplest embodiment, (FIG. 3) the control unit 18 contains a filtering circuit 50 having an input, connected to an output of the receiver device 22 and an output connected to an input of an amplifier limiter 56. An output of the amplifier limiter 56 is an output of the control unit 18 and is connected to a first M-electrode 30 of the electrical stimulator 10. The common buss or system ground is connected to a second M-electrode 30a.

Figure 4:
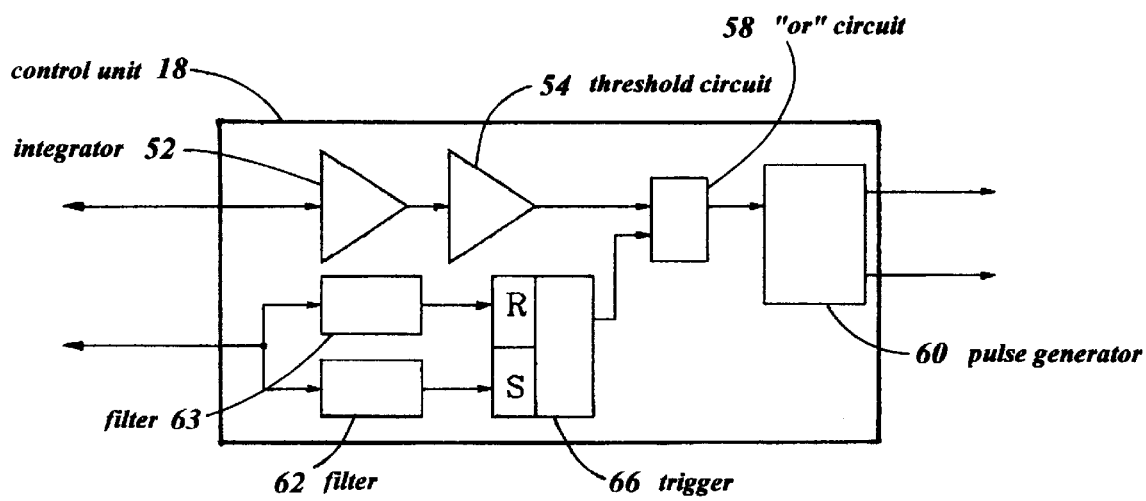
FIG. 4 is a block diagram of the control unit in the embodiment with GIT activity tracking and with external control inputs.

Another embodiment of the control unit 18 (FIG. 4) comprises an integrator circuit 52, an input of which is an input of the control unit 18 and is connected to an output of the receiver device 22. An output of the integrator 52 is connected to an input of threshold circuit 54. An output of the threshold circuit 54 being connected to an input of an "OR"-circuit 58. An output of the "OR"-circuit 58 is connected to a control input of the pulse series generator 60. Outputs of the pulse generator 60 are the outputs of the control unit 18 connected to the M-electrodes 30a which communicates the pulse series to the GIT organs. The control unit 18 contains a first and a second filtering circuits 62 & 63, having a common input from themselves from a second input of the control unit 18. The inputs to the filter circuits 62 & 63 connected in common to a second output of the receiver device 22. A second input of the "OR" circuit 58 is connected to the output of an RS trigger circuit 66. The RS trigger circuit 66 has a "Set" input S which is connected to an output of a filter circuit 62, and a "Reset" input R connected to an output of a filter circuit 63.

In the best embodiment (FIG. 5) the control unit 18 comprises a micro-controller 80, 1 to N analog-digital inputs through amplifiers 82, are connected respectively to 1 to N outputs of the receiver device 22. 1 to M outputs of the micro-controller 80 are connected to corresponding M-electrodes 30 of the electrical stimulator 10. The additional 1 to P outputs of the micro-controller 80, being 1 to P outputs of the control unit 18, are connected to the P-electrodes 46.

The electrical GIT stimulator works as follows. It is introduced into gastro-intestinal tract orally or rectally. Pulse series with average-statistical characteristics are sent from the control unit 18 to the M-electrodes 30a. The receiver device 22 registers data of physiological activity of GIT— i.e. about arising peristaltic waves. These data are transmitted to inputs of the control unit 18. Having achieved sufficiently high motor activity of GIT, which is characterized by certain amplitude and frequency of a voltage, coming from the sensor of pressure or from the sensor of biopotential (criteria of estimation and parameters of pulses are described in the book "Autonomous Electrical Stimulators for Organisms of Humans and Animals" Pekarsky V. V. et al., SMU, Tomsk 1995), i.e. having restored motor evacuative function of GIT or achieved some other effect of electrical stimulation the control unit 18 switches off the pulse series or changes their parameters. A change of parameters of stimulating pulses from average statistical is made when the reaction of GIT organs on electrical stimulation differs from average statistical characteristics, registered for all the period of using electrical GIT stimulators. For example, when having still low motor activity of GIT organs after certain period of stimulation by pulses with average statistical characteristics (current, voltage) it is possible to increase gradually current or voltage of electrical stimulation until a positive effect is achieved. After switching-off pulses or changing their parameters the control unit 18, working under program of micro-controller 80, continues monitoring GIT activity, i.e. the signals coming from internal organs to the receiver device 22 and can, in response to the program, switch on a defined mode of electrical stimulation, and/or connect additional electrodes one by one or in some combination depending on a given program of treatment. Thus, for example, it is possible to carry out electrical GIT stimulation with biocontrol, as it is described by M. A. Sobakin and V. A. Shepelev in their work "Equipment and Methods for Electrical Stomach Stimulation Using a Feedback Principle", /Experimental Surgery and Anesthesiology/—1973 2, p.26. The receiver device 22 registers GIT biopotentials and at each phase of a positive half-wave of GIT biopotentials the control unit 18 sends stimulating pulses to the M-electrodes 30a of the electrical stimulator 10. Using the receiver device 22, with a pH-sensor (acidity sensor), it is possible to track the moving of the electrical stimulator from a stomach with sour environment to bowels with alkaline environment. This is necessary to know for the prescription of electrical stimulation and/or introducing microelements and medicinal preparations into certain sections of GIT. For patients having gastritis, the registration of acidity decrease from pH=1.9 to pH=5.5 is indicative of positive effect achieved from electrical stimulation (see "Autonomous Electrical Stimulators for Organism of Humans and Animals", Pekarsky V. V. et al, SMU, Tomsk 1995, p.68). When the temperature sensor registers an increase in temperature of GIT that is higher than a level of contra-indication for application of electrical stimulation (ibid., p.6), the control unit 18 can, operating under the given program, automatically switch off the electrical stimulator 10. In case of a decrease of GIT activity lower than some defined level, the control unit 18 switches on a pulse series and sends them to the M-electrodes 30a, which are in contact with the GIT walls. The electrical pulses, influence the bowels walls, and cause reciprocal reaction in the form of a peristaltic wave, which moves the electrical stimulator 10 and other contents of the intestine to its diastolic section, where next pulse series is generated and the process repeats.

If, when the capsule is passing certain GIT sections, and there arise pain or muscle convulsions sensations, a patient has an opportunity to switch off the electrical stimulator 10 or to change the parameters of its pulses (to reduce a current or a voltage) using an external transmitter (not shown). The external transmitter may not even be a device, for example, the patient may send switch-on or switch-off signals by clapping himself on abdominal muscles to send a signal to the receiver device 22. This allows removal of muscle convulsions and pain of the patient, thus reducing negative side-effects from use of the offered autonomous electrical GIT stimulator 10. There is also the opportunity for a doctor to monitor the signals received from internal organs and transmitted by the signal transmitter to an external receiver in order to obtain more exact diagnostics and treatment.

The electrical stimulator 10 contains the receiver device 22 for receiving signals from internal organs, and sensors for registering and sending signals of the physiological parameters of motor-evacuative function and condition of the GIT organs. The receiver device 22 can also receive externally transmitted signals. The receiver device 22 can contain a sensor of pressure, a sensor of pressure gradient, pH sensor (acidity sensor), a sensor of background (acoustic) activity, a sensor of biopotential a sensor of conductivity (impedance) of adjoining tissues, a sensor of temperature, etc. The electrical stimulator electrodes, both M-electrodes 30 and P-electrodes 46, can be used for electrodes of the sensor of conductivity of adjoining tissues and for the sensor of biopotential—in which case it is possible to connect the electrodes directly to inputs of the control unit 18 in order to measure conductivity and biopotentials of adjoining tissues. The receiver device 22 contains also a sensor such as an inductor, an acoustic or ultrasound sensor, etc., for receiving external signals or commands sent by an external transmitter. The signals or commands can be transmitted: by radio frequency transmission, inductively, by sound, by ultrasound etc. It is possible to have one sensor for receiving signals from both the internal organs and from the external transmitter (e.g., a sound or audio frequency sensor). 1 to N outputs of the receiver device 22 are connected to 1 to N inputs of the control unit 18, and the circuitry of the receiver device 22 can comprise an amplifier converter, able to amplify and convert the signals from the sensors within the limits, required for reliable work of the control unit 18.

1 to M outputs of the control unit 18 are connected to M-electrodes 30. Likewise, the P-electrodes 46 are connected to separate 1 to P outputs of the control unit 18. The control unit 18, under hardwired control or program algorithm, can switch on or off the pulse series sent to the M-electrodes 30, and additionally change the polarity of the pulse series (bipolarly or monopolarly), including various phase shifts of phases. The control unit 18 can also send pulse series to the P-electrodess 46, and change pulse parameters (current, voltage, duration, frequency, phase of pulses, form, on off time ratio etc.). These changes can be made in response to signals from the internal organs and/or external transmitted signals controlled by the patient or by the doctor. Providing the electrical stimulator 10 with replaceable P-electrodes 46 allows the patient to use P-electrodes 46 with various coatings of microelements or medicinal preparations for different purposes, depending on a specific application of the electrical stimulator 10, or on a doctor's prescription or recommended therapeutic program. The electrodes of the offered stimulator 10 should be made from non-toxic, biologically neutral materials, which are stable in an aggressive environment (for example, from stainless steel). Also, certain electrodes can be integral to the casing 12 as a constructive element, or can be designed as a conducting film covering the casing 12 of an electrically insulated capsule. The form of the electrodes should provide for good contact with adjoining muscle tissues of the GIT. The casing 12 of the electrical stimulator should be streamline, suitable for safe application orally, rectally, or for vaginal use. The casing 12 should provide tightness both of the electronic circuit, and of the power source 4, and must be made from a non-toxic, biologically neutral material (i.e., food impervious).

The electrical GIT stimulator 10 contains the signal transmitter 14, having 1 to N inputs which are connected to 1 to N outputs respectively of the receiver device 22, and an input connected to a separate output of the control unit 18. The information transmitted from the transmitter 14 is accepted by an external receiver (not shown) for medical supervision and diagnostics. The same channels may be used for sending information to external transmitter and receiving external commands from it; possibly the same sensor may be utilized—for example an ultrasonic sensor or acoustic microphone can generate ultrasonic or sound oscillations, which can be accepted by the external receiver, in the same way it is possible to use an inductive coil.

In an embodiment having external control (FIG. 3), the control unit 18 contains a filter circuit 50, the input of which is connected to an output of the receiver device 22. The output of the filter circuit 50 is connected to an input of the amplifier limiter 56, the output of which is in turn connected to an M-electrode 30a of the electrical stimulator 10, and its common buss or ground is connected to another M-electrode 30a. The filtering circuit 50 separates an effective signal coming from an external transmitter, and the amplifier limiter 56 amplifies and restricts the parameters of pulse series within required limits (for example, current no more than 10 mA).

The embodiment of the control unit 18 (FIG. 4) having GIT activity tracking and external control comprises an integrator 52, controlling a pulse series generator 60, which, for example, may be a series circuit of multi-vibrators forming pulse series. An example of such a pulse generator is a microcircuit I106A, utilized in autonomous electrical GIT stimulation. The control unit 18 can operate under a hardwired algorithm, where, having achieved high GIT motor activity the pulses (voltage), the receiver device 22, registering characteristics of GIT motor activity (for example, pressure or biopotentials) sends an input signal to the integrator 52. The output of integrator 52 is connected to an input of the threshold device (comparator) 54. When high GIT motor activity is sensed, the voltage at the output of the integrator circuit 52 reaches a threshold level and the threshold circuit 54 switches off the pulse series generator 60 by way of the first input to the "OR" circuit 58, an output of which is connected to the control input of the pulse series generator 60. Upon a decrease of GIT motor activity, the voltage at an output of the integrator 52 is reduced below the threshold level and the threshold circuit 54 switches on the pulse series generator 60. In this embodiment, a first filtering circuit 62 separates a switch-on signal of the electrical stimulator 10, and a second filtering circuit 63 separates a switch-off signal of the stimulator 10. Their outputs are connected respectively to the Set and Reset input of the RS trigger circuit 66. The output of the trigger circuit 66 is connected to a second input of the "OR" circuit 58. Upon receipt from the second output of the receiver device 22 of a signal from an external transmitter to switch-on or switch-off the electrical stimulator 10, the corresponding filtering circuit 62 or 63 sets or resets the RS trigger circuit 66, and through the second input of the "OR" circuit 58 switches on or off the pulse series generator 60.

Figure 5:
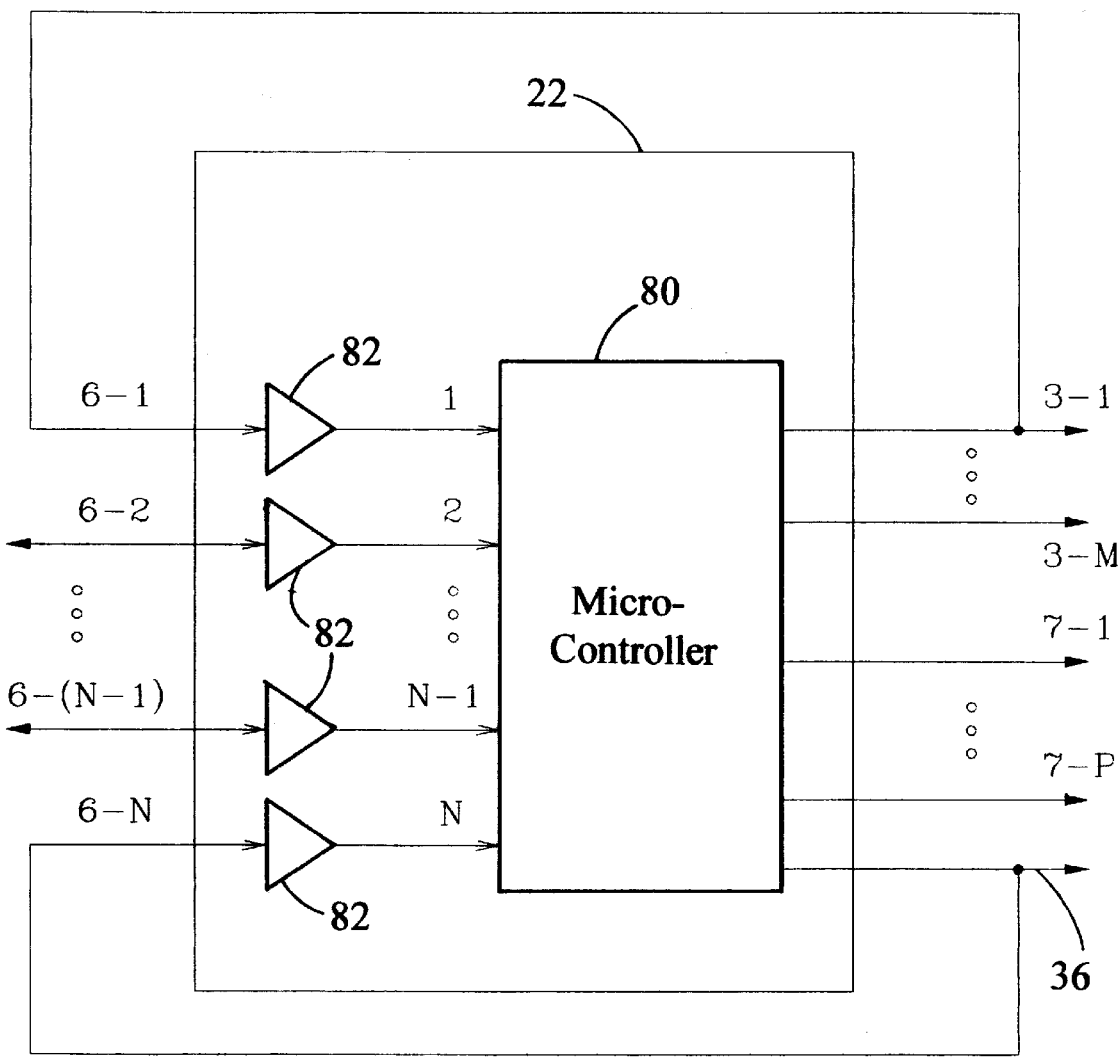
FIG. 5 is a block diagram of the control unit in the embodiment with multichannel tracking for condition of GIT organs and for receiving signals of external control for correlation with parameters of electrical stimulation.

In the preferred embodiment of FIG. 5, the control unit 18 is embodied as a micro-controller 80, which comprises a microprocessor, program and data memory, analog to digital converters, digital to analog converters, discrete inputs/outputs, and timer (not shown). Examples for accomplishing such a micro-controller include microcircuits PIC16!71 of the Microchip firm, 83!51GB or 87C196KB of the Intel firm (see the reference book "One crystal micro-ECM" Moscow: MIKAP, 1994, p. 391). The signals from internal organs and/or an external transmitter from 1 to N outputs of the receiver device 22 come through amplifiers 82 to 1 to N analog-digital inputs of the micro-controller 80. The response parameters of how the algorithms of the micro-controller 80 react on receiving these signals, are input into the micro-controller 80 with the help of a program. The program is installed in the micro-controller 80 either at the stage of manufacturing, or at the stage of pre-selling preparation, or directly by the consumer before use. In this embodiment, the M-Substitute electrode 30a of the electrical stimulator 10 for communicating pulse series to the GIT organs are also used for sensing biopotential. The biopotential signals from an M-electrode 30a pass through the amplifier 20 to the 1st analog-digital input of the micro-controller 80. The signal sensor of the external transmitter is combined with the signal transmitter connection 36, which is carried out as an acoustic microphone, output of which through an amplifier 82 is connected to N analog-digital input of the micro-controller 80. For the electrical stimulation of adjoining tissues, M-electrodes 30 are connected 1 to M outputs of the micro-controller 80. Additional P-electrodes 46 are connected separate 1 to P outputs of the micro-controller 80.

INDUSTRIAL APPLICABILITY

The offered electrical GIT stimulator 10, in comparison with uncontrollable autonomous electrical GIT stimulators, reduces or eliminates side-effects, such as a pain and muscle convulsions, caused by the passage of the electrical stimulator 10 through certain GIT sections. The offered stimulator 10 also improves treatment efficiency owing to the ability to select exact electrical stimulation parameters, and to select exact microelements or medicinal preparations dose to the specific GIT section by an electrochemical means. Providing replaceable electrodes allows treatment of patients differentially, i.e., to prescribe electrodes preparations with one or another coating of microelements or medicinal preparations and their combinations, depending on character of disease. Also the offered stimulator 10 is economically favorable to the consumer, since there is an opportunity to buy separately for the stimulator 10 replaceable preparation electrodes with various coatings of microelements or medicinal preparations under a prescription of the doctor, or under recommendations of medical programs, depending on character of application of the electrical stimulator 10. There is also an option for supervision by the treating doctor of the condition of the patient based on signals coming from internal organs and transmitted by the signal transmitter 14 to an external receiver. The offered electrical GIT stimulator 10 can be successfully applied to treatment and prevention of various diseases in abdominal surgery (post operating paresis, peritonitis, gall systems pathology, complicated forms of stomach ulcer and duodenum diseases), in intensive therapy and reanimation of persons with acute poisonings, for treatment of therapeutic type diseases (gastritis, non complicated stomach ulcer and duodenum diseases, chronic opistorhozes, disease of gall ways and large intestines, chronic constipation). The offered electrical GIT stimulator 10 does not require unique technologies and is realized on an integrated components basis using standard technologies of hybrid integrated circuits.

After description of embodiments of the offered invention with the reference to applied drawings it is clear, that the present invention is not limited only by these embodiments and the various changes and up dating that could be carried out by one of skill in the art without a deviation from the main problem, which is defined in applied items of the formula.

What is claimed is:

1. An electrical gastro-intestinal tract stimulator comprising a casing with M-electrodes, the casing in the form of a medicinal capsule, containing a power source, a control unit having outputs which are connected to the M-electrodes, and a device for receiving signals having outputs which are connected to N inputs of the control unit, wherein the device for receiving signals further comprises sensors for sensing physiologic parameters of motor-evacuative function and current condition of gastro-intestinal tract organs and for receiving signals from an external transmitter.

2. The electrical stimulator of claim 1, wherein the device for receiving signals further comprises at least one sensor selected from the group consisting of: a sensor of pressure, a sensor of a pressure gradient, a pH-sensor, an acoustic sensor, a sensor of temperature, a sensor of signals from an external transmitter, a sensor of biopotential, and a sensor of conductivity.

3. The electrical stimulator of claim 1, further comprising a signal transmitter having N-inputs which are connected to N-outputs of the device for receiving signals and the control unit.

4. The electrical stimulator of claim 1, further comprising P-electrodes with a coating of microelements or medicinal preparations.

5. The electrical stimulator of claim 4, further comprising means for demounting the P-electrodes from the stimulator.

6. The electrical stimulator of claim 4, wherein the control unit further comprises a micro-controller having analog-digital amplifiers as inputs, inputs of which amplifiers are inputs of the control unit and are connected to outputs of the device for receiving signals, and the micro-controller having M outputs being outputs of the control unit connected to the M-electrodes and to the P-electrodes of the electric stimulator.

7. The electrical stimulator of claim 1, wherein the control unit further comprises a filtering circuit having an input which is an input of the control unit connected to an output of the device for receiving signals and having an output connected to an input of an amplifier-limiter circuit, and the amplifier-limiter circuit having an output which is an output of the control unit and is connected to a first of said M-electrodes of the electrical stimulator and a common buss connected to a second of said M-electrodes of the electrical stimulator.

8. The electrical stimulator of claim 1, wherein the control unit further comprises an integrator having an input which is a first input of the control unit and is connected to a first output of the device for receiving signals and having an output connected to an input of a threshold circuit, the threshold circuit having an output connected to a first input of an "or" circuit, the "or" circuit having an output connected to a control input of a pulse series generator, the pulse series generator having outputs which are outputs of the control unit and are connected to the M-electrodes, a first and a second filtering circuits having a common input which is a second input of the control unit connected to a second output of the device for receiving signals the first filtering having an output connected to a set input of an RS-trigger circuit and the second filtering having an output connected to a reset input of the RS-trigger circuit, and the RS trigger circuit having an output connected to a second input of the "or" circuit.

9. An in-dwelling electrical gastro-intestinal tract stimulator system including gastrointestinal tract sensors, external receivers and transmitters and an in-dwelling electrical gastro-intestinal tract stimulator, said stimulator comprising:
   a casing configured in the form of a medicinal capsule and constructed to be biocompatible with the gastro-intestinal tract;
   an electronic stimulator circuit disposed within the casing, the stimulator circuit for electrically stimulating the gastro-intestinal tract and comprising:
      an electrical power source for powering a control unit, a receiver device and a transmitter device of the stimulator circuit by means of an electrical connection, a control unit for controlling the stimulator circuit, the control unit electrically connected to a set of electrical stimulator electrodes, the electrical stimulator electrodes mounted proximate a surface of the casing, and to the receiver device, and to a transmitter device, a receiver device for receiving signals, and having electrical connections for outputting signals to the control unit and to a transmitter device, and a transmitter device being electrically connected to the receiver device and to the control unit, the transmitter device for sending signals to an external receiver.

10. The stimulator of claim 9, wherein the receiver device of the stimulator circuit receives at least one signal from a sensor of a physiological parameter indicative of motor-evacuative function of the gastro-intestinal tract, the parameter selected from the group consisting of pressure, pressure gradient, pH, sound, temperature, biopotential, conductivity, and any other parameter indicative of gastro-intestinal tract status.

11. The stimulator of claim 9, wherein the signal transmitter of the stimulator circuit receives inputs from the receiver device and the control unit.

12. The stimulator of claim 9, wherein said electrodes further comprises P-electrodes mounted proximate the surface of the casing, the P-electrodes having a coating selected from the group consisting of microelements and medicinal preparations, and being electrically connected to the control unit.

13. The stimulator of claim 9, wherein said electrodes comprises P-electrodes which are demountable.

14. The stimulator of claim 9, wherein the control unit of the stimulator circuit comprises:

a filtering circuit having an input and an output, the input for receiving signals from the receiver device; and an amplifier-limiter circuit having an input, an output and a common buss, the input connected to the filtering circuit and the output connected to a first of said electrical stimulator electrode and the common buss connected to a second of said stimulator electrode.

15. The stimulator of claim 9, wherein the control unit of the stimulator circuit comprises:

an integrator circuit having an input connected to a first output of said electrical connections for outputting signals of the receiver device and an output connected to an input of a threshold circuit;

the threshold circuit having an output connected to an OR circuit;

the OR circuit having first and second inputs and an output, the first input connected to the output of the threshold circuit, the second input connected to an output of an RS-trigger circuit, and the output connected to an input of a pulse generator;

a pulse generator having a control-input connected to the output of the OR circuit, and outputs connected to said set of electrical stimulator electrodes;

a first and a second parallel filtering circuits, having a common input connection to a second output of the receiver device, and the first filtering circuit having an output connected to a SET-input of the RS-trigger circuit, and the second filtering circuit having an output connected to a RESET-input of the RS-trigger circuit; and the RS-trigger circuit having the SET-input and RESET-input each separately connected to the output of the first and second filtering circuits, and the output connected to the second input of the OR circuit.

16. The stimulator of claim 9, wherein the control unit comprises:

amplifiers 1 to N, each having an input connected to a signal source selected from the group consisting of a feed-back circuit, the receiver device and the transmitter device, and each having a digital output connected to an input of a microprocessor; and a microprocessor, having N-inputs 1 to N, and M-outputs 1 to M and P-outputs 1 P, and the M-outputs being connected to said electrical stimulator electrodes, and the P-outputs being connected to a set of P-electrodes.

17. The control unit of claim 16, wherein the amplifiers 1 to N further comprise analog-digital converters.

18. The stimulator of claim 9, wherein the receiver device of the stimulator circuit receives an externally transmitted signal.

19. An electrical gastro-intestinal tract stimulator device capable of being introduced into the gastro-intestinal tract orally or rectally or suitable for vaginal use, comprising:

a casing in the form of a capsule with M-electrodes and P-electrodes and containing a power source; a control unit having N-inputs, M-outputs and P-outputs, and the M-outputs connected to the M-electrodes, and the P-outputs connected to the P-electrodess provided with a coating of microelements or medicinal preparations; a receiver device for receiving signals from internal organs and an external transmitter, and having the N-outputs connected to the N-inputs of the control unit; and a signal transmitter device for sending signals from the receiver device and the control unit to an external receiver for medical observation and monitoring.

* * * * *